(12) United States Patent
Lowe et al.

(10) Patent No.: US 8,715,748 B2
(45) Date of Patent: May 6, 2014

(54) METHODS FOR INHIBITING PROSTATE CANCER BY KINASES AND ANGIOGENESIS INHIBITORY MECHANISMS OF BALL MOSS EXTRACT

(71) Applicants: Henry Lowe, Kingston (JM); Joseph L. Bryant, Baltimore, MD (US)

(72) Inventors: Henry Lowe, Kingston (JM); Joseph L. Bryant, Baltimore, MD (US)

( * ) Notice: Subject to any disclaimer, the term of this patent is extended or adjusted under 35 U.S.C. 154(b) by 0 days.

(21) Appl. No.: 13/910,692

(22) Filed: Jun. 5, 2013

(65) Prior Publication Data

US 2013/0323330 A1 Dec. 5, 2013

Related U.S. Application Data

(60) Provisional application No. 61/655,694, filed on Jun. 5, 2012.

(51) Int. Cl.
*A01N 65/00* (2009.01)
(52) U.S. Cl.
USPC ............................................. 424/725

(58) Field of Classification Search
None
See application file for complete search history.

(56) References Cited

U.S. PATENT DOCUMENTS 7,713,556 B2   5/2010   Lowe

OTHER PUBLICATIONS

A. Jemal et al., Global Cancer Statistics, Ca. Cancer J. Clin. 2011; 61: 69-90 (Mar.-Apr. 2011).

*Primary Examiner* — Michael Meller
(74) *Attorney, Agent, or Firm* — Ober, Kaler, Grimes & Shriver; Royal W. Craig

(57) ABSTRACT

A method of treating prostate cancer by administering a pharmaceutically-acceptable amount of a crude extract of the indigenous Jamaican plant Ball Moss (*Tillandsia Recurvata*) comprising one or more cycloartane isolates, and the isolates used in the method for eliciting thereby a kinase inhibitory response of prostate cancer cells by selectively inhibiting MRCKα kinase and angiogenesis of (growth of new blood vessels) to reduce the viability of prostate cancer cells. The method and compounds holds promise as a chemopreventive agent, without causing excessive damage to normal cells.

5 Claims, 5 Drawing Sheets

Cycloartanes identified by LC-MS in ball moss (*Tillandsia recurvate L.*)

FIG. 10

Bioactivity profile of Ball Moss and its cycloartanes and analogs against Prostate cancer cell lines and associated kinases

| Compound | Bioactivity ($\mu M$ or $\mu g/ml$) | | Angiogenis inhibition | Kinase inhibition ($kd_{50}$ - $\mu M$ or $\mu g/ml$) | | | | |
|---|---|---|---|---|---|---|---|---|
| | PC-3 | DU-145 | | MRCKα | MRCKβ | MEK5 | GAK | DRAK1 |
| Ball Moss extract ($\mu g/ml$) | 5.97±4.99 | - | | - | - | 12 | 8 | 12 |
| Cycloartane-3,24,25-triol | 2.22± 0.28 | 1.67 ± 0.18 | | 0.26 | | - | - | - |
| Cycloart-23-ene-3,25-diol | 2.38 | 1.864 | | 0.21 | | | | |
| Cycloart-25-ene-3,25-diol | | | | | | | | |
| 3,23-Dioxo-9,19-cyclolanost-24-en-26-oic acid | | | | | | | | |
| Cycloeucalenol | | | | | | | | |
| 24,25-Dihydroxycycloartan-3-one | | | | | | | | |
| Hydroxycycloart-23-en-3-one,25, | | | | | | | | |
| Sterculin A | | | | | | | | |

FIG. 11

METHODS FOR INHIBITING PROSTATE CANCER BY KINASES AND ANGIOGENESIS INHIBITORY MECHANISMS OF BALL MOSS EXTRACT

CROSS-REFERENCE TO RELATED APPLICATION(S)

The present application derives priority from U.S. provisional application Ser. No. 61/655,694, filed 5 Jun. 2012.

BACKGROUND OF THE INVENTION

1. Field of the Invention

The present invention relates to anti-cancer drugs and, more particularly, to a method for inhibiting prostate cancer by kinases and angiogenesis inhibitory mechanisms of a class of cycloartanes extracted from Ball Moss (*Tillandsia Recurvata*).

2. Description of the Background

There is great growth in the overlapping fields of biology, technology, and medicine, including remarkable advances in cellular biology that have given a new understanding of the molecular basis for some diseases. Nevertheless, the incidence of some forms of cancer continues to rise. This is particularly true of prostate cancer, a leading cause of death in men. Indeed, prostate cancer is the second most frequently diagnosed cancer and sixth leading cause of cancer death in males worldwide. A. Jemal et al., Global Cancer Statistics, Ca Cancer J Clin 2011; 61:69-90 (March-April 2011).

The three conventional treatment options include surgery, radiation and chemotherapy, or some combination of the three. Chemotherapy is the most widely used tool in prostate cancer treatment especially where the cancer has metastasized or spread to other organs of the body. However, conventional chemotherapy is not specific to cancer cells and has serious toxic side effects. Moreover, in recent years prostate cancer cells have exhibited increased resistance to current chemotherapies. Consequently, there exists an urgent need to discover and develop new therapeutics that can slow the growth of cancer cells while having lesser side effects on the patients. The search for new molecules to combat the rising cases of prostate cancer especially those resistant to current chemotherapy calls for urgent action.

The more recent development of target therapies for the treatment of human cancers is revolutionizing the concept of cancer treatment today and has led to a profusion of drugs to treat cancer patients. These drugs include alkylating agents, intercalating agents, antimetabolites, etc., most of which target DNA or enzymes regulating the DNA duplication and elongation process. However, rapidly growing tumors do not always exhibit high levels of cell proliferation, but may also exhibit low levels of cell death compared to the normal cell population from which these tumor cells issue. For these types of rapidly growing tumors, the mentioned drugs are not effective. In addition, like chemotherapy, the great majority of the drugs currently available for treatment of cancer are toxic and involve detrimental side-effects on healthy cells, tissues and organs. Targeted anticancer therapies rely on compounds that interfere with cellular targets, e.g., they inhibit molecular targets that play a pivotal role in tumor progression. Such therapies specifically target the cancer cells, thus minimizing toxicity. A number of such target-based anticancer therapies are now successfully used in routine clinical practice.

A kinase is an enzyme that activates or inactivates certain proteins that control several biological activities in the cell including cell growth, proliferation, apoptosis (programmed cell death) and metabolism. There are two main types of kinases: those that phosphorylate tyrosine residues and those that phosphorylate serine and/or threonine residues in target proteins. The latter, protein kinase inhibitor's, may be categorized by the amino acids whose phosphorylation is inhibited. The body uses kinases extensively to transmit signals and control complex processes in cells, and myriad different kinases have been identified in humans. In the event of carcinogenesis, eukaryotic cells become predisposed to rapid and uncontrollable growth. This is evidenced by elevated levels of different kinases expressed in various cancers. It is for this reason that kinase inhibitors hold promise in restoring normal cell proliferation and may provide a key cancer treatment. Consequently, in recent years kinase inhibitors have emerged as major targets for therapeutics, particularly for cancer related therapies. However, relatively few kinase inhibitors have been identified to date and so effort is being made to discover new molecules that interact with kinases. A number of kinase inhibitors such as Gefitinib (Approved for Non-Small Cell Lung cancer) have shown promise in clinical trials against prostate cancer. Most of the other kinase inhibitors in clinical trial (3 in Phase III) against prostate cancer targets kinases that inhibits angiogenesis. Tumor angiogenesis is the formation of new blood vessels which supplies cancer cells with nutrients and oxygen. Antiangiogenic agents work by cutting off blood supply to tumors thus starving cancer cells to death.

A tyrosine kinase is an enzyme that can transfer a phosphate group from ATP to a protein in a cell. Tyrosine kinase functions as an "on" or "off" switch in many cellular functions. It can become mutated, stuck in the "on" position, and cause unregulated growth of the cell, which is a necessary step for the development of prostate cancer. Numerous tyrosine kinase inhibitors have proven to be effective antitumor agents and anti-leukemic agents. For example, in chronic myelogenous leukemia, the Abelson tyrosine kinase inhibitor Imatinib (Gleevec™) targets the activity of BCR-ABL oncoprotein; in acute promyelocytic leukemia (APL), all-trans-retinoic acid (ATRA) or arsenic trioxide ($As_2O_3$) targets PML-RARα fusion. The introduction of ATRA or Imatinib in the treatment of APL or chronic myelogenous leukemia patients has significantly improved the management of these diseases.

An effective tyrosine kinase inhibitor must be capable of killing or incapacitating prostate cancer cells without causing excessive damage to normal cells. Elevated levels of LIMK1 kinase are expressed in prostate cancer, a kinase which itself is activated by MRCKα. Inhibitors of the MRCKα kinase may restore normal cell proliferation and provide a key solution to cancer treatment. Medicinal plants have been one of the major sources for the discovery of a number of current clinically used anticancer drugs.

Jamaica is known for its rich biodiversity and its abundant usage of medicinal plants as ethno medicines. *Tillandsia recurvata* L. (Bromeliaceae) which is commonly called the Jamaican Ball Moss or the Old Man's beard is one of the several important plants found in Jamaica. Several countries report its use in their ethnomedicine. The major reported use is in Brazil where the plant is used against rheumatism, ulcers and hemorrhoids. Previous phytochemical studies showed the presence of; five hydroperoxyclycloartanes, a dicinnamate, a flavanone and a caffeic acid ester from the whole plant extracts.

In his U.S. Pat. No. 7,713,556 issued May 11, 2010, one of the inventors named herein investigated the anti-tumor and anti-inflammatory properties of a silica acid moiety extract of Jamaican Ball Moss.

The present inventors have found that a class of cycloartane isolates from the indigenous plant selectively inhibits MRCKα kinase and angiogenesis of (growth of new blood vessels) to reduce the viability of prostate cancer cells. The extract holds promise as a chemopreventive agent.

SUMMARY OF THE INVENTION

It is, therefore, the primary object of the present invention to provide a method for inhibiting prostate cancer by administering a pharmaceutically-acceptable amount of a crude extract of the indigenous Jamaican plant Ball Moss (*Tillandsia Recurvata*) containing one or more cycloartane isolates to elicit a kinase inhibitory and/or angiogenesis inhibitory response of prostate cancer cells, without causing excessive damage to normal cells.

The selected class of cycloartane phytochemicals derived from Jamaican Ball Moss produces promising anti-cancer and anti-inflammatory activity by selectively inhibiting MRCKα with greater potency than other potential chemotherapeutics, and actually reduces the viability of several prostate cancer cell lines.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 10 is a chart listing all twenty-two cycloartane type triterpenoid compounds isolated from the crude extract.

FIG. 11 is a chart of the kd50 kinase interactions.

DETAILED DESCRIPTION OF THE PREFERRED EMBODIMENTS

The present invention is a therapeutic cycloartane extract derived from plant biomass, and more specifically the indigenous Jamaican plant Ball Moss (*Tillandsia Recurvata*), for use in regressing cancerous tumors and/or for anti-inflammatory effect, as well as the method for inhibiting prostate cancer by administering a pharmaceutically-acceptable amount of the crude extract to elicit a kinase inhibitory and/or anti-angiogenic response against prostate cancer cells without causing excessive damage to normal cells.

Preparation of the Ball Moss Extracts

The whole *Tillandsia Recurvata* plant was collected by hand from trees and electricity poles at Kingston, Jamaica. A voucher specimen of the plant was identified at the Institute of Jamaica Herbarium where it is deposited with Accession Number: IJ 3411. The collected plant material was air dried under shade, pulverized into powder, and extracted. extracted at room temperature for 48 hours in the dark with 95% ethanol followed by $CH_2Cl_2$. Following the addition of water to the ethanol extract, a further extraction was carried out in hexane. The hexane extract was combined with the $CH_2Cl_2$ extract and evaporated to dryness resulting in a green residue (8.55 g). 3.32 g of the residue was fractionated by dry column flash chromatography on Si gel using hexane/$CH_2Cl_2$/ethyl acetate and mixtures of increasing polarity yielding 9 fractions (F1-F9). Degassing was done by ultra-sonication of the samples to yield an insoluble solid, which solid was then filtered. The fractions were subjected to high performance liquid chromatography (HPLC) using a column Phenomenex Luna™ C18, 5 μm, 2×50 mm; eluent, acetonitrile with 0.05% MeOH. This confirmed the presence of the cycloartanes in all 9 fractions.

Select Class Of Cycloartane Phytochemicals

The inventors undertook to identify the phytochemicals responsible for the observed anti-cancer and anti-inflammatory activities in ball moss and to further isolate these phytochemicals. Identification of the various components was based on liquid chromatography/mass spectroscopy (LC/MS) ions as correlated to literature data. Several molecular weight matches cycloartane compounds as well as a triterpene, sterculin-A, were observed in the extracts as described below. Proton Nuclear Magnetic Resonance Spectroscopy (1H-NMR) was performed and the interpreted spectra were consistent with steroid-like structures.

Figure 1:
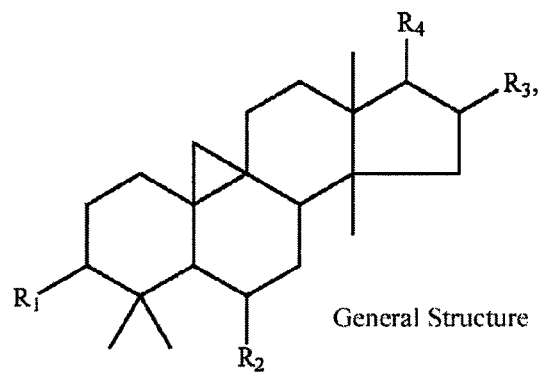
FIG. 1 is the general structural formula of the cycloartane phytochemicals according to the present invention.

The identified compounds are in the general class of cycloartane type triterpenoid compounds of Formula I (below), also shown in FIG. 1:

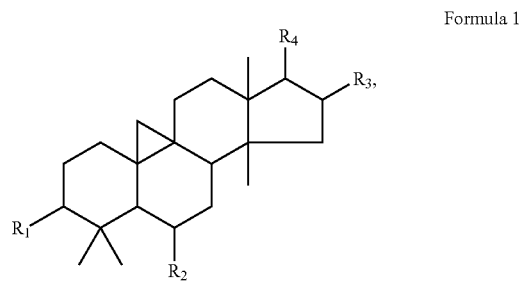

Formula 1

In Formula I, R1 is OH, O2, $H_2C$ or $O_2C$, R2 is H, R3 is H, and R4 is any one of Formulas 2-9:

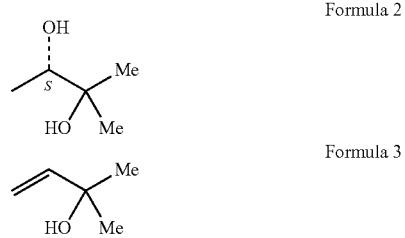

Formula 2

Formula 3

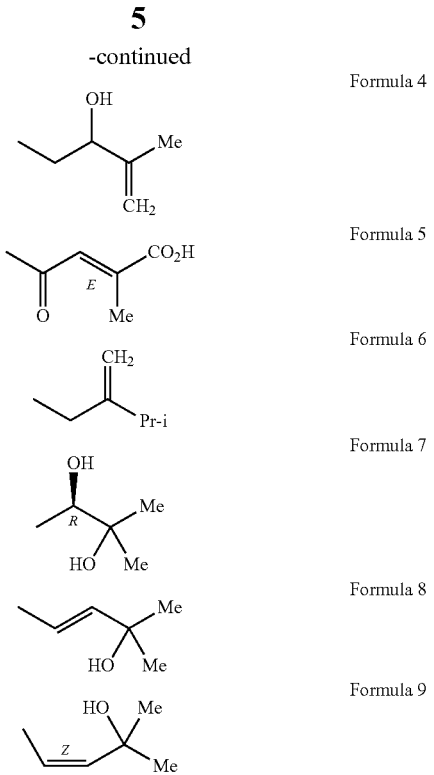

Figure 2:
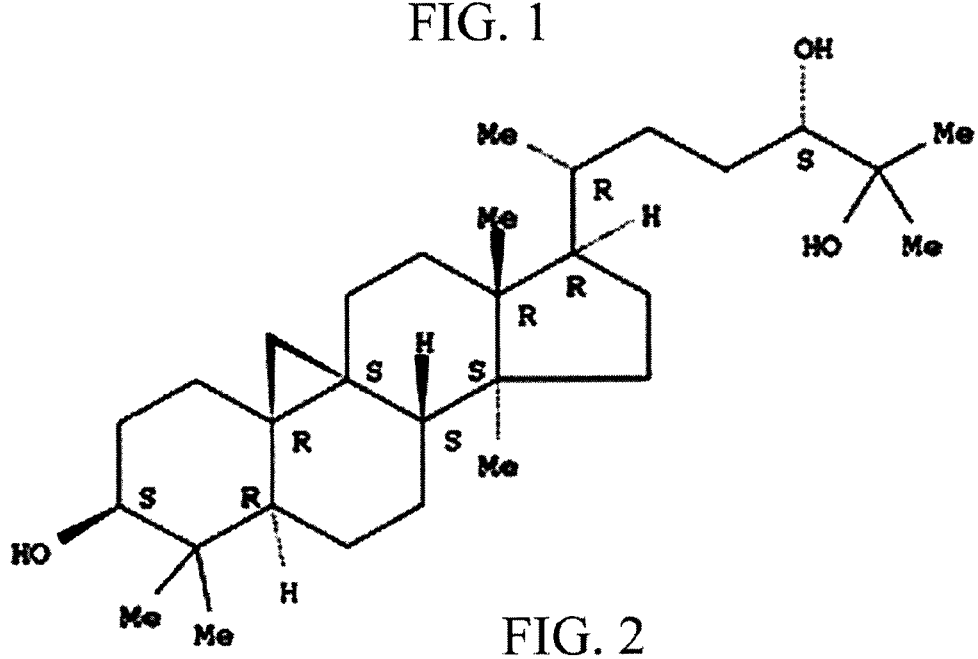
FIG. 2 is the structural formula for the cycloartane phytochemical Cycloartane-3,24,25-triol according to the invention.
Figure 3:
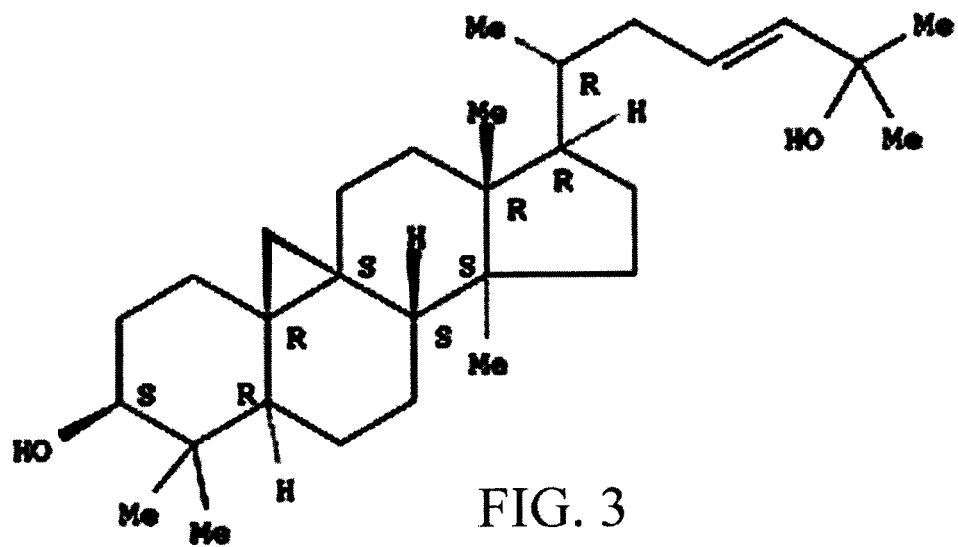
FIG. 3 is the structural formula for the cycloartane phytochemical Cycloart-23-ene-3,25-diol according to the invention.
Figure 4:
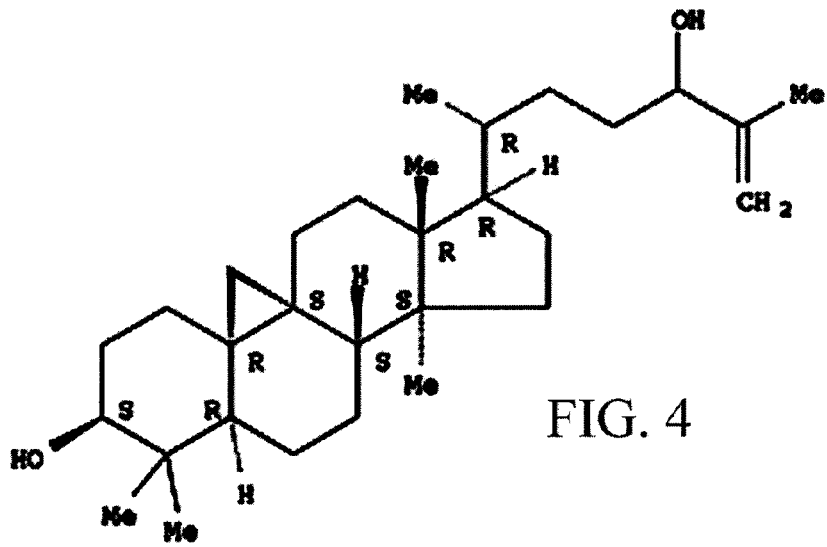
FIG. 4 is the structural formula for the cycloartane phytochemical Cycloart-25-ene-3,25-diol according to the invention.
Figure 5:
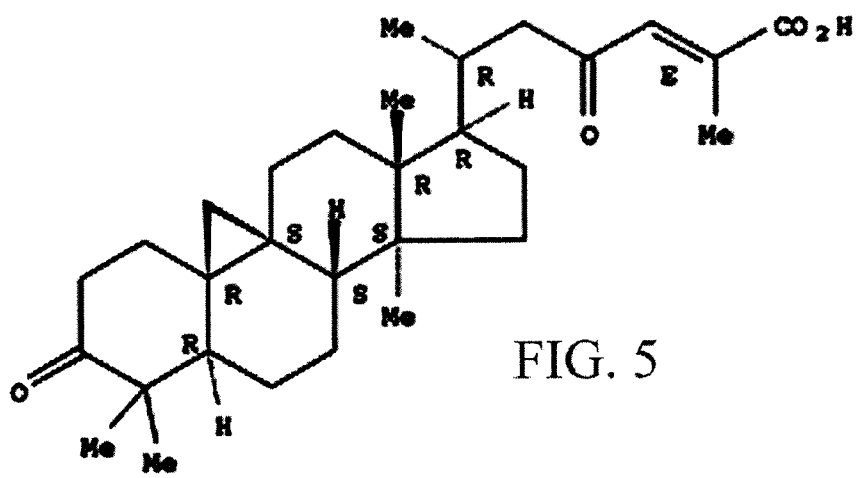
FIG. 5 is the structural formula for the cycloartane phytochemical 3,23-Dioxo-9,19-cyclolanost-24-en-26-oic acid according to the invention.
Figure 6:
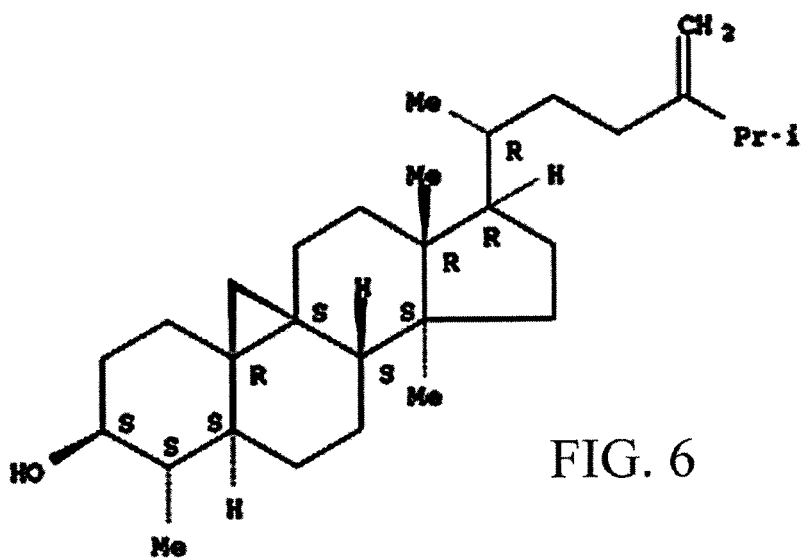
FIG. 6 is the structural formula for the cycloartane phytochemical Cycloeucalenol according to the invention.
Figure 7:
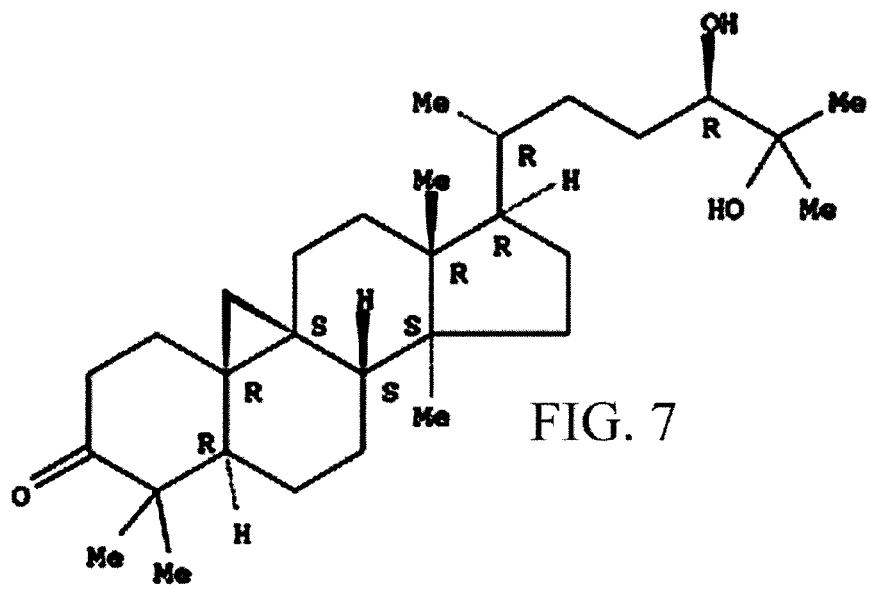
FIG. 7 is the structural formula for the cycloartane phytochemical 24,25-Dihydroxycycloartan-3-one according to the invention.
Figure 8:
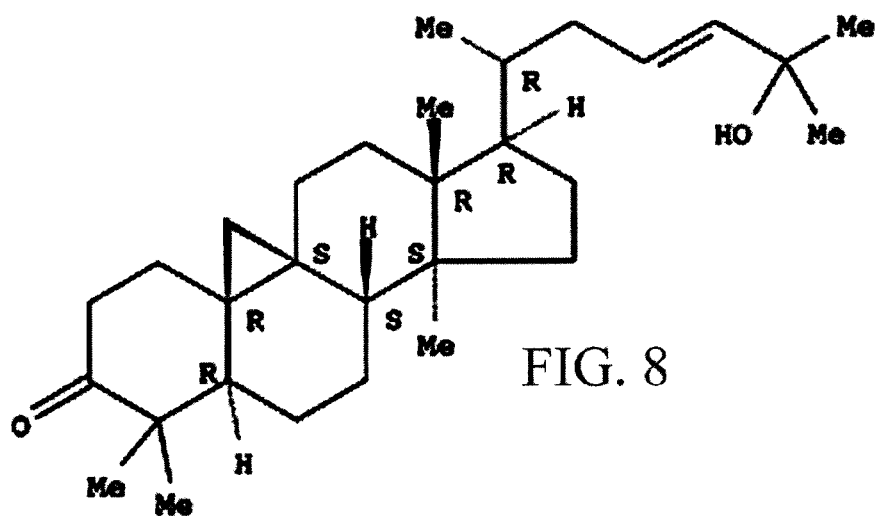
FIG. 8 is the structural formula for the cycloartane phytochemical Hydroxycycloart-23-en-3-one,25 according to the invention.
Figure 9:
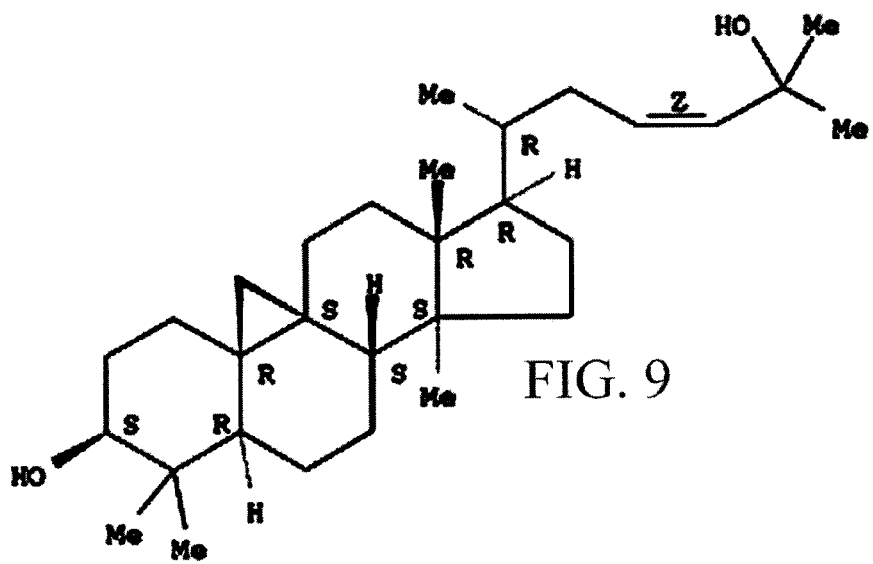
FIG. 9 is the structural formula for the cycloartane phytochemical Sterculin A according to the invention.

In all twenty-two cycloartane type triterpenoid compounds were isolated in the crude extract. All twenty-two cycloartane type triterpenoid compounds are illustrated in FIG. 10. Of these, eight are shown in FIGS. 2-9, respectively, and are characterized as follows:

FIG. 2: Cycloartane-3,24,25-triol
FIG. 3: Cycloart-23-ene-3,25-diol
FIG. 4: Cycloart-25-ene-3,25-diol
FIG. 5: 3,23-Dioxo-9,19-cyclolanost-24-en-26-oic acid
FIG. 6: Cycloeucalenol
FIG. 7: 24,25-Dihydroxycycloartan-3-one
FIG. 8: Hydroxycycloart-23-en-3-one,25,
FIG. 9: Sterculin A Test Results The crude *Tillandsia Recurvata* biomass extracted above were tested in cell lines PC-3 and DU145 to determine their antiprostate cancer activity as well as the interaction of the crude extract against 451 kinases, as were the Cycloartane-3, 24,25-triol and Cycloart-23-ene-3,25-diol isolates. The cells (PC-3 and DU145) were maintained in minimum essential media (MEM) supplemented with 10% fetal calf serum (FCS), 20 mMl-glutamine, 2% penicillin-streptomycin, and 0.2% gentamicin. Cells were maintained at 37° C. with 5% $CO_2$ in Corning 75 cm3 culture flasks. Cells were trypsinized and plated at the appropriate density (500-2000 cells/well in log phase 72 h post drug addition) into 96 well plates in media for approximately 18 h after which they were exposed to cycloartanes; cycloart-23-ene-3,25-diol and cycloartane, cycloart-23-ene-3,25-triol for 72 h. The compounds were solubilized in DMSO (>0.1%). Following the appropriate treatments, cell proliferation was measured using the WST-1 (4-[3-(4-iodophenyl)-2-(4-nitrophenyl)-2H-5-tetrazolio]-1, 3-benzene disulfonate) (Roche) colorimetric assay according to the manufacturer's instructions. All assays were performed in duplicates and were monitored spectrophotometrically at 450 nm/690 nm (Synergy™ HT 96-well Plate Reader-BIO-TEK). Cell viability was assessed as percent of drugs relative to vehicle solvent-treated control.

IC50 values were determined from the extract dose versus control growth curves using Graph Prism software.

Competition binding assays were established, authenticated and executed. For most assays, kinases were fused to T7 phage strains and for the other assays, kinases were produced in HEK-293 cells after which they were tagged with DNA for quantitative PCR detection. In general, full-length constructs were used for small, single domain kinases, and catalytic domain constructs for large multi-domain kinases. The binding assays utilized streptavidin-coated magnetic beads treated with biotinylated small molecule ligands for 30 minutes at room temperature which generated affinity resins for the kinase assays. The liganded beads were blocked with excess biotin and washed with blocking buffer to remove unbound ligand and to reduce non-specific phage binding. Binding reactions were assembled by combining kinases, liganded affinity beads, and test compounds in binding buffer. Test compounds were prepared as 40× stocks in 100% DMSO and diluted directly into the assay (Final DMSO concentration=2.5%). All reactions were performed in polypropylene 384-well plates in a final volume of 0.04 ml. The assay plates were incubated at room temperature with shaking for 1 hour and the affinity beads were washed. The beads were then re-suspended in elution buffer and incubated at room temperature with shaking for 30 minutes. The kinase concentration in the eluates was measured by quantitative PCR and FIG. 11 presents kd50 for kinase interaction with the test compound. These were determined using a standard dose response curve using the hill equation. Curves were fitted using a non-linear least square fit with the Levenberg-Marquardt algorithm.

The crude Ball Moss extract showed potent kinase inhibitory activity against five kinases, four of which are implicated in prostate cancer growth and spread. The *Tillandsia Recurvata* biomass extract also shows antiangiogenic activity in an ex-vivo Rat Ring Aorta assay. These results demonstrate that a pharmaceutically-acceptable amount of 8-14 µg/ml of the crude extract of the indigenous Jamaican plant: Ball Moss (*Tillandsia Recurvata*) elicits a pharmaceutically-effective kinase inhibitory response of prostate cancer cells without causing excessive damage to normal cells.

Similar results were observed with the two tested isolates, and similar results are expected with the remaining isolates. These results validate the anti-tumor activity of the ball moss crude extract and its isolates, as well as their mechanism of action being anti-angiogenesis which can also be deemed chemopreventive. These results, makes crude *Tillandsia Recurvata* (Ball Moss) extract containing any one or more of the above-identified isolates a very good candidate for development into a prostate cancer treatment. More studies are currently underway to confirm the ability of Ball Moss to halt the growth of prostate tumors in mice as well as measure the inhibitory effects of the crude extract on the 4 related kinases and antiangiogenic effects in vivo.

These natural isolates will prove useful in drug design aimed at treating selected cancers with fewer side effects as well as being anti-inflammatory agents. Of course, one skilled in the art will understand that any of the cycloartane isolates described above can be prepared by chemical synthesis as opposed to isolation from their natural source, and the synthetic equivalents and their analogs are also considered to be within the scope and spirit of the invention.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A method of treating prostate cancer in a human in need thereof consisting essentially of administering to said human a therapeutically effective amount of a hexane extract of Jamaican Ball Moss to effectively treat said prostate cancer in said human.

2. The method of claim 1 wherein said hexane extract contains a cycloartane phytochemical having the following chemical formula:

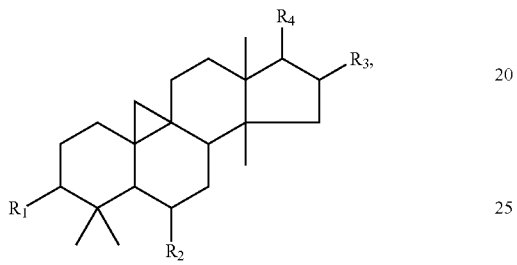

where R1 is OH, O2, H$_2$C or O$_2$C, R2 is H, and R3 is H.

3. The method according to claim 2, wherein R4 is any one from among a group consisting of the following formula 2-9:

Formula 2

Formula 3

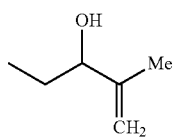

Formula 4

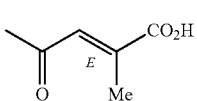

Formula 5

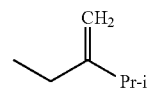

Formula 6

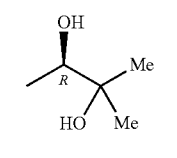

Formula 7

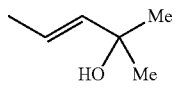

Formula 8

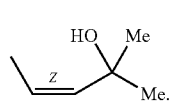

Formula 9

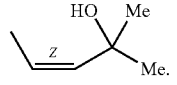

4. The method according to claim 2, wherein said cycloartane phytochemical contains a cycloartane triterpenoid compound.

5. The method according to claim 2, wherein said cycloartane phytochemical is a compound selected from the group consisting of Cycloartane-3,24,25-triol, Cycloart-23-ene-3,25-diol, Cycloart-25-ene-3,24-diol, 3,23-Dioxo-9,19-cyclolanost-24-en-26-oic acid, Cycloeucalenol, 24,25-Dihydroxycycloartan-3-one, Hydroxycycloart-23-en-3-one, 25, sterculin A and mixtures thereof.

* * * * *